United States Patent [19]
Hargett, Jr. et al.

[11] Patent Number: 6,136,276
[45] Date of Patent: Oct. 24, 2000

[54] FLEXIBLE VESSEL AND FRAME FOR MICROWAVE ASSISTED CHEMISTRY

[75] Inventors: Wyatt Price Hargett, Jr., Matthews; James Edward Thomas, Harrisburg; Matthew Donald Barrett, Charlotte, all of N.C.

[73] Assignee: CEM Corporation, Matthews, N.C.

[21] Appl. No.: 09/482,453

[22] Filed: Jan. 13, 2000

Related U.S. Application Data

[63] Continuation of application No. 09/062,858, Apr. 20, 1998.

[51] Int. Cl.$^7$ ...................................................... B01L 3/00
[52] U.S. Cl. ........................ 422/102; 422/102; 422/104; 422/113; 436/155
[58] Field of Search ................................ 422/21, 22, 102, 422/104, 113; 436/155

[56] References Cited

U.S. PATENT DOCUMENTS

| | | |
|---|---|---|
| 4,493,444 | 1/1985 | Del Bon et al. . |
| 4,672,996 | 6/1987 | Floyd et al. . |
| 4,882,128 | 11/1989 | Hukvari et al. . |
| 5,264,185 | 11/1993 | Floyd . |
| 5,270,010 | 12/1993 | Lautenschlaeger . |
| 5,345,066 | 9/1994 | Knapp et al. . |
| 5,369,034 | 11/1994 | Hargett et al. . |
| 5,427,741 | 6/1995 | Bennett . |
| 5,520,886 | 5/1996 | Bennett et al. . |

FOREIGN PATENT DOCUMENTS

| | | |
|---|---|---|
| 0416759 | 3/1991 | European Pat. Off. . |
| 0830891 | 3/1998 | European Pat. Off. . |
| 99/13979 | 3/1999 | WIPO . |

OTHER PUBLICATIONS

Lorentzen, M.L., et al., "Comparison of Microwave–Assisted and Conventional Leaching Using EPA Method 3050B," Analytical Chemistry, vol. 68, No. 24, Dec. 15, 1996, pp. 4316–4320.

*Primary Examiner*—Long V. Le
*Assistant Examiner*—Kathryn Bex
*Attorney, Agent, or Firm*—Philip Summa, P.A.

[57] ABSTRACT

A self venting sealable vessel system for microwave assisted chemistry is disclosed. The system includes a vessel formed of a microwave-transparent material, one end of which forms an opening for placing materials inside the vessel, a lid for being seated against the opening, a flexible frame surrounding the vessel and lid and formed of a microwave-transparent material, and means for urging the frame against the vessel and seated lid with a predetermined force to seal the vessel at low pressures and so that the frame refrains from flexing until the pressure inside the vessel exceeds the predetermined force, after which the frame flexes sufficiently to allow the lid to unseat and gases to vent safely from the vessel without rupturing the vessel or the frame.

17 Claims, 5 Drawing Sheets

FLEXIBLE VESSEL AND FRAME FOR MICROWAVE ASSISTED CHEMISTRY

This application is a continuation of Ser. No. 09/062,858 filed Apr. 20, 1998.

FIELD OF THE INVENTION

The present invention relates to microwave assisted chemistry techniques and apparatus, and in particular, relates to an apparatus that provides a safe and efficient release of pressure generated in closed vessels by chemical reactions that are microwave assisted.

BACKGROUND OF THE INVENTION

The term "microwave assisted chemistry" refers to the use of electromagnetic radiation within the microwave frequencies to provide the energy required to initiate, drive, or accelerate certain chemical reactions. As chemists have long been aware, the application of heat energy is one of the most significant factors in increasing the rate of a wide variety of chemical reactions. Thus, generally familiar devices such as the Bunsen burner, other types of gas burners, hot plates, and other similar devices have historically been used to initiate or accelerate various chemical reactions.

As a relatively crude comparison, microwave assisted chemistry techniques are used to heat chemical reagents in the same way that a consumer microwave oven cooks food. There are significant differences, however, between the ordinary consumer use of microwave energy with food and its laboratory use with chemical reagents. Thus, the devices and techniques required for microwave assisted chemistry are generally much more sophisticated than are the consumer-oriented devices and techniques.

In one comparison, however, a laboratory microwave device and a consumer microwave offer the same advantage: in many circumstances they both greatly increase the rate at which materials can be heated as compared to the rates that they could be heated by ordinary conduction or convection heating. Thus, microwave assisted chemistry has been particularly valuable in driving or accelerating reactions that tend to be time-consuming under more conventional heating techniques. Particular examples include moisture analysis, in which samples must effectively be heated to dryness; digestion, a process in which a chemical composition is broken down into its elements for further analysis, with the breakdown generally being accomplished by heating the composition in one or more mineral acids; and the Kjeldahl techniques for nitrogen determination. Using conventional heating techniques, moisture analysis, Kjeldahl, or digestion reactions can be very lengthy, extending for hours in some cases. When the reactions are microwave assisted, however, they can be completed in a much shorter period of time. It will be understood that this time savings has a particularly significant advantage in any situation in which large number of samples must be tested on an almost continuous basis. Thus, although microwave assisted chemistry is relatively new compared to some other techniques, it has become well established and accepted in a number of analytical applications.

As well understood by those familiar with the electromagnetic spectrum, the term "microwave" is often used generically to refer to radiation with wavelengths of between about 1000 and 500,000 microns ($\mu$), and corresponding frequencies of between about $1\times10^9$ and $5\times10^{11}$ Hertz (Hz). These are arbitrary boundaries, however, and other sources refer to microwaves as having frequencies of between about $10^8$ Hz and $10^{12}$ Hz and wavelengths of between about 300 centimeters (cm) and 0.3 millimeters (mm). For commercial and consumer purposes in the United States, the available microwave frequencies are regulated by the Federal Communications Commission and are generally limited to certain frequencies such as 2450 megahertz (MHz). Because of the relatively long wavelength of microwave radiation, microwave assisted chemistry techniques are often carried out in closed vessels which are in turn placed inside a device that bears a superficial relation to a consumer microwave oven, but that is much more sophisticated in its source, waveguide, cavity, and control elements.

In turn, because the reactions are often carried out inside closed vessels, and because the reactions often generate gas, the reactions tend to generate and build up significant pressure in the reaction vessels. Accordingly, vessels have been developed to withstand most expected pressures, and also to include various pressure relief devices to prevent the vessels from exploding under the significant pressures being generated. An exemplary vessel and pressure release system is set forth, for example in U.S. Pat. No. 5,369,034, which is assigned to CEM Corporation of Matthews, N.C.

In many of these existing vessels systems, however, the pressure release function destroys or consumes, even if intentionally, a part of the vessel system (e.g., a rupture disc). Thus, even though such parts are intended to be easily replaced, doing so can represent a disadvantage in certain circumstances.

Accordingly, in more recent attempts at solving the problem, vessels have been designed in which the venting mechanism is more permanent. One example is U.S. Pat. No. 5,270,010 to Lautenschlager. In this device, a domed spring with a particular structure is used to help hold the lid on a pressure vessel for microwave assisted chemistry. It has been found in actual practice, however, that the performance of the spring degrades over time, particularly under the high pressures experienced by these vessels. Thus, although the domed spring does not need to be replaced every time the vessel vents gases, it does have to be replaced on a regular basis.

OBJECT AND SUMMARY OF THE INVENTION

Therefore, the need exists for vessels for microwave assisted chemistry that can release pressure in a satisfactory manner and a controlled manner, but without destroying either a replaceable or more permanent part of the vessel. It is an object of the present invention to provide such vessels.

The invention meets this object with a self-venting sealable vessel system that comprises a vessel formed of a microwave transparent material, one end of which forms an opening for placing materials inside the vessel. A lid is seated against the opening, and a flexible frame surrounds the vessel and lid and is similarly formed of a microwave transparent material. The vessel system includes means for urging the frame against the vessel and the seated lid with a predetermined force to seal the vessel at low pressures and so that the frame refrains from flexing until the pressure inside the vessel exceeds the predetermined force, after which the frame flexes sufficiently to allow the lid to unseat and gases to vent safely from the vessel without rupturing the vessel or the frame.

The foregoing and other objects and advantages of the invention and manner in which the same are accomplished will become clearer based on the following detailed description taken in conjunction with the accompanying drawings in which:

DETAILED DESCRIPTION OF THE INVENTION

Figure 1:
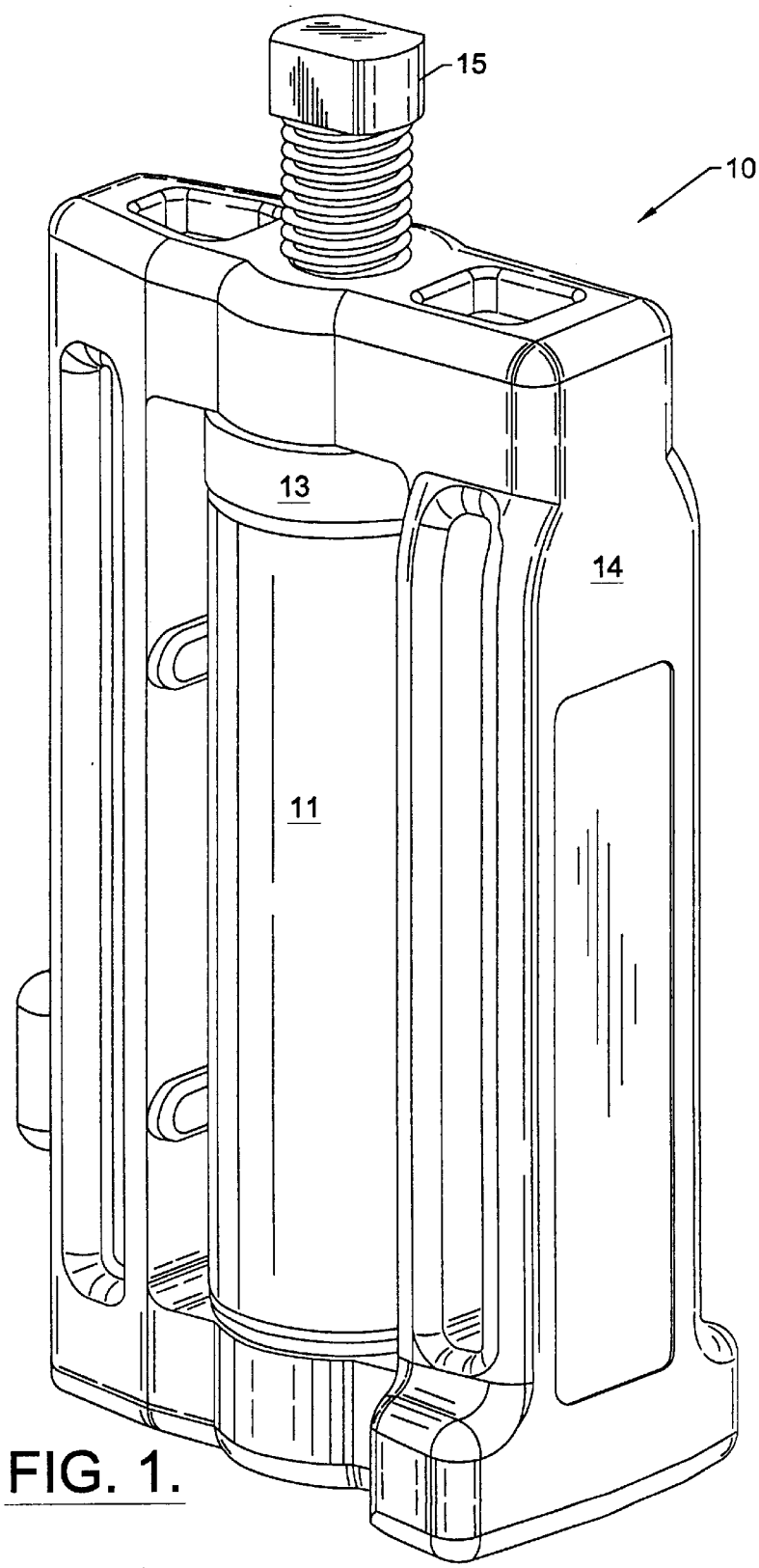
FIG. 1 is a perspective view of a vessel system according to the present invention.

FIG. 1 is a perspective view of a vessel system according to the present invention and broadly designated at 10. In its broadest aspects, the invention comprises a vessel 11 formed of a microwave transparent material, one end of which forms an opening 12 (FIG. 2) for placing materials inside the vessel. A lid 13 is seated against the opening 12.

A flexible frame 14 surrounds the vessel 11 and lid 13 and is similarly preferably formed of a microwave transparent material. Means shown as the bolt 15 urge the frame 14 against the vessel 11 and the seated lid 13 with a predetermined force to seal the vessel at low pressures and so that the frame 14 refrains from flexing until the pressure inside the vessel 11 exceeds the predetermined force, after which the frame 14 flexes sufficiently to allow the lid 13 to unseat from the vessel 11 and for gases to vent safely from the vessel 11 without rupturing the vessel 11 or the frame 14.

The term "flexible" is, of course, relative. With respect to the present invention, the term refers to a frame that is dimensionally stable under normal conditions and not easily deformed. The frame will, however, flex without breaking under more severe forces; i.e., at bout 500 psi for certain materials and up to 1500 psi for other materials. Materials that will begin flexing at such pressures, particularly polymeric materials, are well understood in the art. Thus, the composition and structure of the frame can be selected without undue experimentation.

Selecting the desired flexibility of the frame thus defines the internal pressure at which the frame will flex and the vessel self-vent.

As FIG. 1 further illustrates, in preferred embodiments the vessel 11 is cylindrical and the frame 14 is rectangular, although it will be understood that other shapes could be used without departing from the scope of the invention or the claims.

Figure 2:
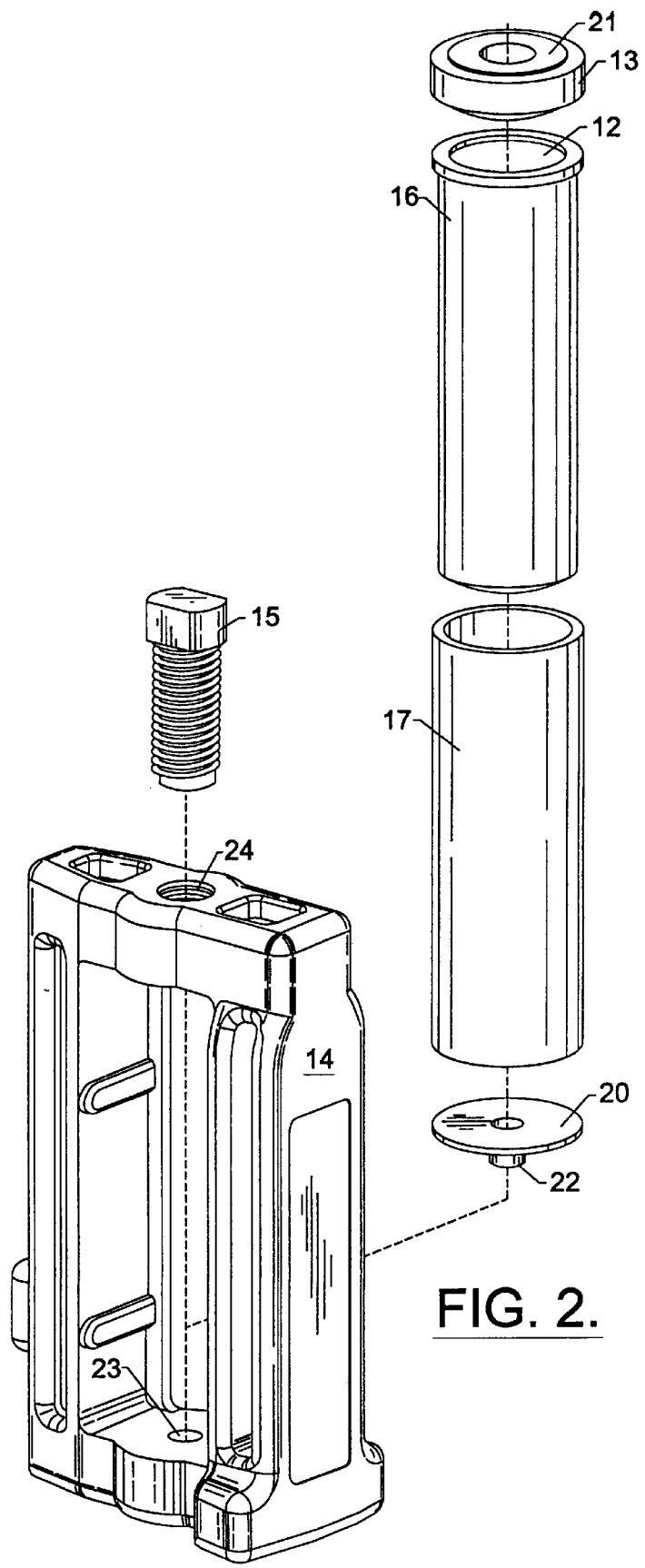
FIG. 2 is an exploded perspective view of the system illustrated in FIG. 1.
Figure 3:
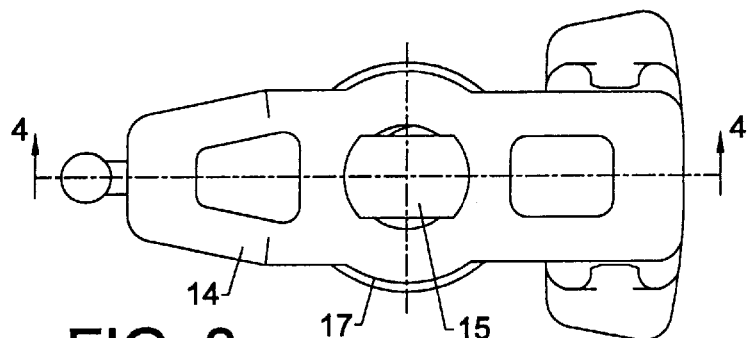
FIG. 3 is a top plan view of a vessel system according to the present invention.
Figure 4:
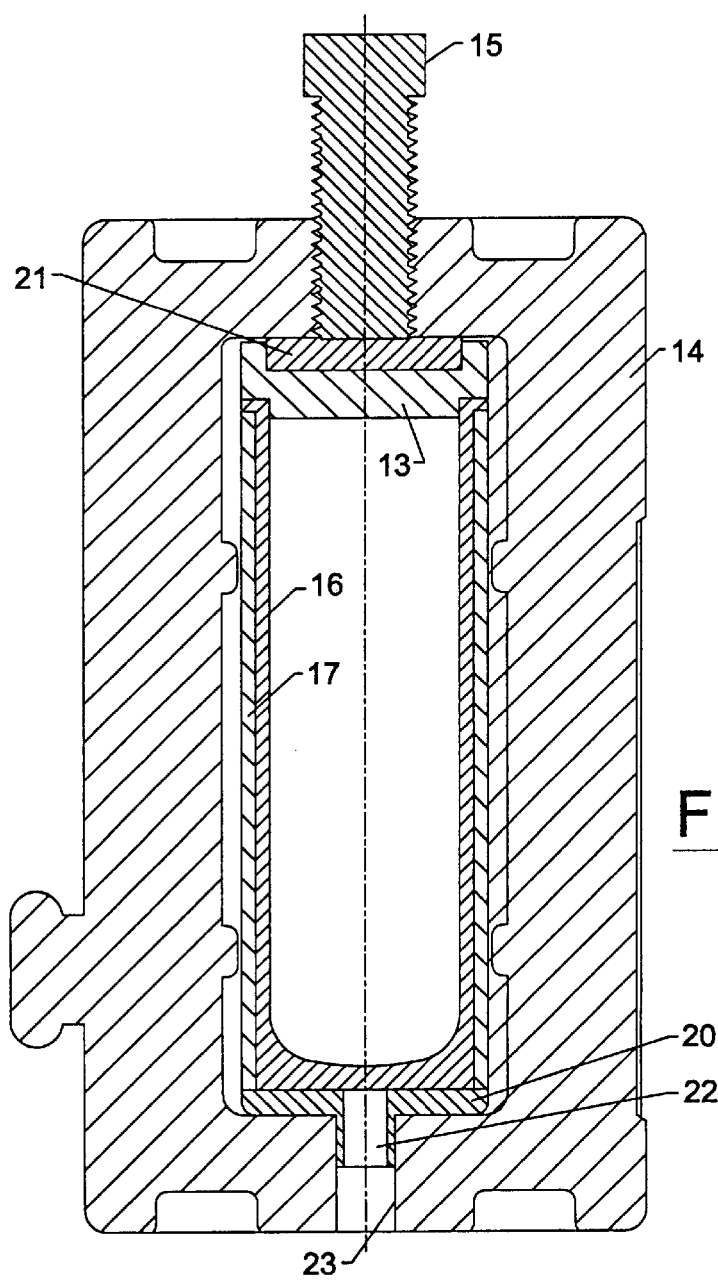
FIG. 4 is a cross-sectional view taken along lines 4—4 of FIG. 3.

FIG. 2 illustrates that in preferred embodiments, the vessel 11 is formed of an inner liner 16 formed of a microwave transparent and chemically resistant material, and a pressure resistant reinforced outer sleeve 17 with one end of the inner liner 16 forming the mouth 12 for placing materials inside the vessel. The lid 13 is also formed of a microwave transparent chemically resistant material for being seated against the opening 12 and for closing the vessel 11. In preferred embodiments, the inner liner 16 and the lid 13 are formed of materials that include tetrafluoroethylene polymers, glass, or quartz. It will be likewise understood that the term "chemically resistant" is necessarily relative, and that it refers herein to a material that resists attack from the chemical compositions that are expected to be placed therein, or to form as a reaction proceeds therein.

When the lid 13 is formed of a relatively flexible material (at least under the expected pressures) such as PTFE, the invention further preferably comprises a stiffening member 21 for being externally seated against the lid 13. FIG. 2 illustrates a particularly preferred embodiment in which the stiffening member 21 is a circular disc that fits inside an identically sized circular recess in the lid 13. Thus, when combined, the lid 13 provides the microwave transparency and chemical resistance required for microwave assisted chemistry, while the stiffening member 21 provides the strength required to keep the vessel closed under desired pressure conditions.

The embodiment illustrated in FIG. 2 further includes another seating member 20 which can be positioned at the opposite end of the vessel from the lid 13. FIG. 2 illustrates that the seating member 20 can include a self-locating pin or nub 22 that fits into a corresponding opening 23 in the frame 14.

In both FIGS. 1 and 2 it will be understood that the frame is formed of a material and with a size sufficient to give it a particularly desired strength so that it refrains from flexing until a sufficient pressure inside the vessel is reached. The frame along with the stiffening member and the seating member 20 are thus typically selected from the group consisting of high-strength thermoplastic polymers and engineering polymers. Typical polymers include, but are not limited to, ABS resins, acrylic resins, nylon, PEEK resins, phenolformaldehyde resins, polybutylene terephthalate, polycarbonate, higher strength polyethylene, polypropylene, and polystyrene, polyvinylchloride (PVC), and urea formaldehyde resins. Particularly preferred plastics are the polyether imide plastics such as ULTEM™ from General Electric. Thermoplastic materials can be made with varying strengths by a number of polymerization and catalyzation techniques that are well understood by those in the polymer arts and will not be otherwise repeated herein. In general, however, it will be understood that if the desired venting pressure is to be about 500 pounds per square inch (psi), the engineering plastic selected for the frame 14, and the frame's design, will be less rigid than that selected for the extremely high pressure vessels for which the frames need to remain rigid until pressures of about 1500 psi are reached.

Both FIGS. 1 and 2 illustrate that the means for urging the frame against the vessel, as well as the stiffening member and lid against the vessel, comprises a threaded opening 24 in the top portion of the frame 14 and the threaded bolt 15 that engages the opening 24. It will be understood that as the bolt 15 is tightened in the opening 24, it urges the stiffening member 21 against the lid 13 and the lid 13 against the inner sleeve 16 and liner 17 and against the seating member 20 to preload the frame and vessel with the desired force. This force with which the vessel and frame are preloaded is either equal or proportional to the pressure at which it is thus desired for the vessel to vent. In this manner, the invention provides a simple yet elegant technique for self venting the vessel at particular desired pressures.

The inner liner 16 can be formed of a polymer (e.g., PTFE), PFA perfluoroalkoxy resins), glass, or quartz, as may be desired or necessary depending upon the reactions to be carried out therein.

In preferred embodiments, the outer sleeve 17 is formed of a braided structure of fiberglass yarns such as is available from CEM Corporation of Matthews, N.C., the assignee of the present invention, in conjunction with their MARS 5™ systems. Alternatively, the vessel can be reinforced in a manner set forth, for example, in commonly assigned U.S.

Pat. Nos. 5,427,741 and 5,520,886, the disclosures of which are incorporated entirely herein by reference.

The invention also offers advantages, however, for lower-pressure reactions in which pressure-driven safety venting is less of a concern. For example, microwave-assisted techniques are useful in solvent extraction procedures. These tend to take place at lower pressures, but because organic extraction solvents tend to be both volatile and flammable, these techniques require that the vessels remain sealed against vapor release. Under these circumstances, the frame 14 and the bolt 15 provide the means for tightly sealing extraction reactions even at lower pressures. Stated differently, the vapor pressures generated during solvent extraction are generally insufficient to threaten the physical integrity of the vessel. Nevertheless, the escape of hot organic vapors could present an entirely different set of problems, and is preferably avoided.

It will be further understood that the invention is particularly useful when a group of vessels are used concurrently in a microwave cavity so that multiple reactions can be carried out at the same time. Thus, in another preferred embodiment, the invention further comprises a source of microwave radiation, a cavity in microwave communication with the source, and a plurality of the vessel systems 10 in the cavity. The use of a plurality of vessels in a single cavity is well understood and illustrated in the art and will not be otherwise described herein or in the drawings.

Figure 5:
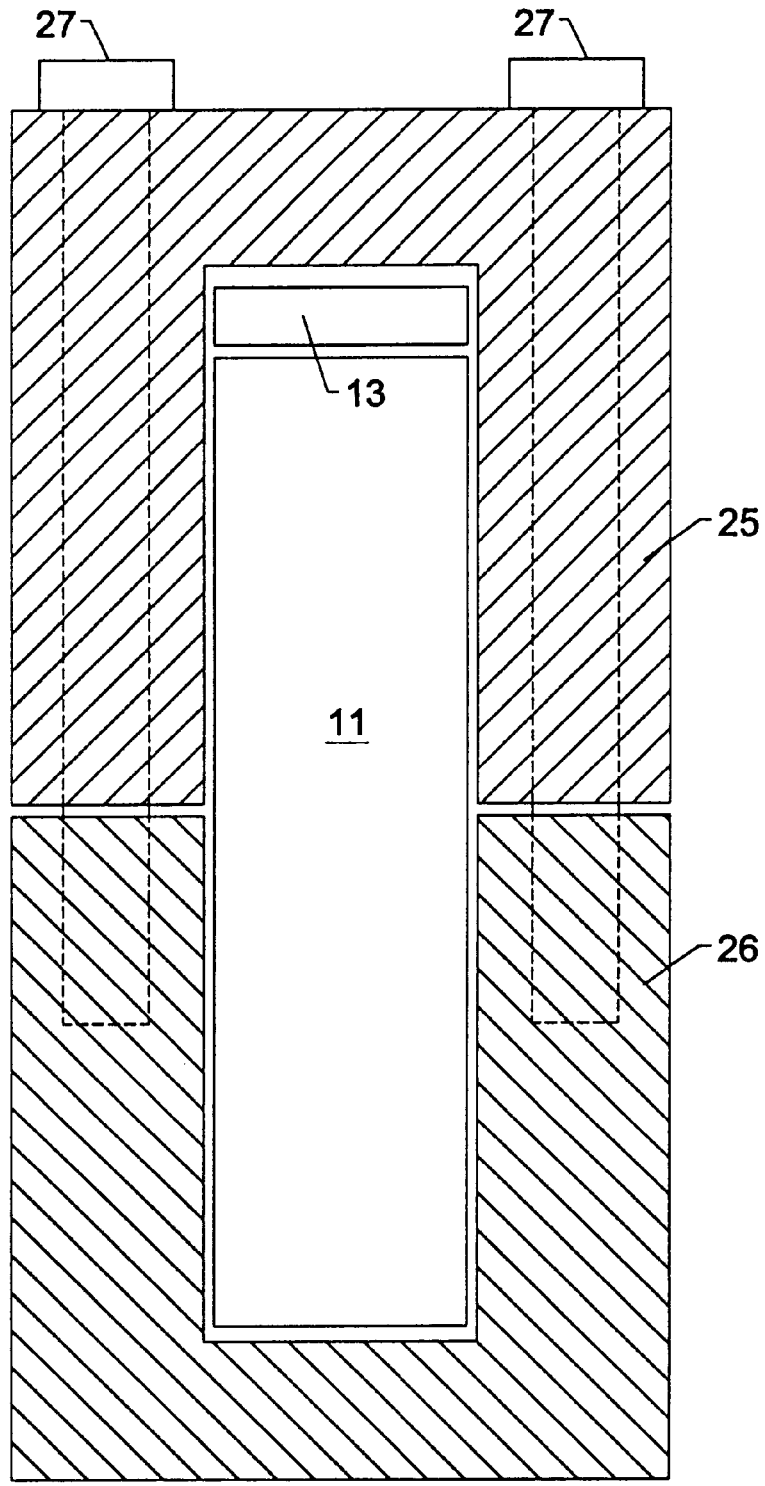
FIG. 5 is a cross-sectional view of a second embodiment of the invention.
Figure 6:
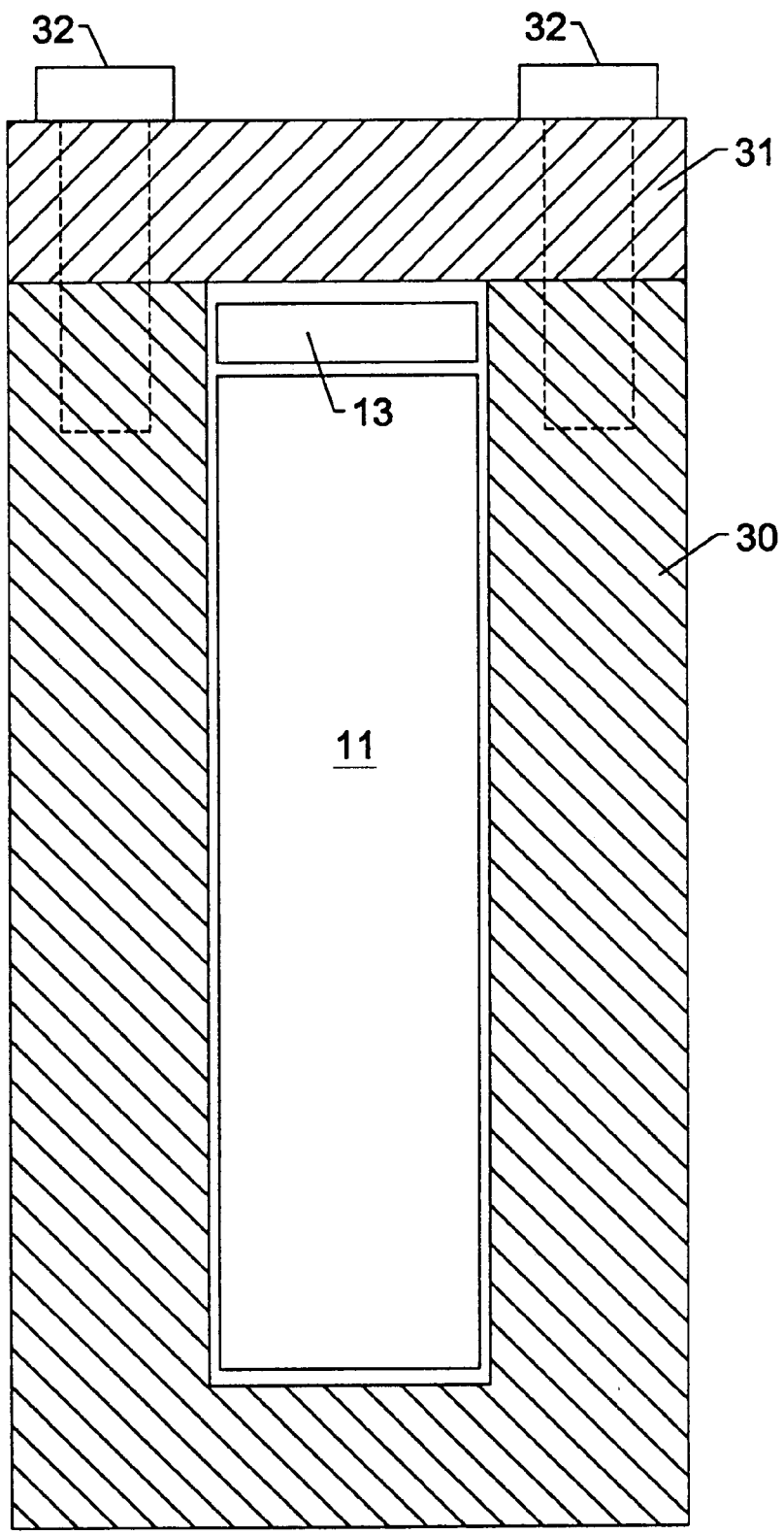
FIG. 6 is another cross-sectional view of a third embodiment according to the present invention.

FIGS. 5 and 6 illustrate other embodiments in which the frame comprises a plurality of portions that can be fastened together in a manner that urges the frame against the vessel and thus urges the lid and the vessel against each other.

In FIG. 5, the vessel is again shown at 11 and the lid at 13, although in somewhat less detail than in the earlier drawings. The frame, however, comprises two complementing U-shaped portions 25 and 26 which can be fastened together with the bolts 27. It will thus be seen that the combination of the frame portions 25 and 26 and the tightening bolts 27 urges the frame against the vessel 11 and the vessel and the lid 13 against each other in the same manner as does the frame 14 and bolt 15 illustrated in FIGS. 1–4.

FIG. 6 illustrates yet another embodiment in which the frame comprises a large U-shaped portion 30 and a capping portion 31, the two of which are urged against one another and against the vessel 11 and lid 13 by another set of bolts 32. It will be understood that in FIGS. 5 and 6 the vessel 11 and lid 13 can be complemented by the sleeve and stiffening member arrangements illustrated in FIGS. 1–4. It will likewise be understood that other physical arrangements can be used to clamp or otherwise urge a frame against a vessel and its lid in a manner entirely consistent with the present invention and equivalent thereto.

In the drawings and specification, there have been disclosed typical embodiments of the invention, and, although specific terms have been employed, they have been used in a generic and descriptive sense only, and not for purposes of limitation, the scope of the invention being set forth in the following claims.

That which is claimed is:

1. A self venting sealable vessel system for microwave assisted chemistry and comprising:
    a vessel formed of a microwave-transparent material, one end of which forms an opening for placing materials inside said vessel;
    a lid for being seated against said opening;
    a flexible frame surrounding said vessel and lid and formed of a microwave-transparent material; and
    means for urging said frame against said vessel and seated lid with a predetermined force to seal said vessel at pressures at or below said predetermined force and so that said frame refrains from flexing until the pressure inside said vessel exceeds said predetermined force, after which said frame flexes sufficiently to allow said lid to unseat and gases to vent safely from said vessel without rupturing said vessel or said frame.

2. A self venting vessel system according to claim 1 comprising a cylindrical vessel and a rectangular frame.

3. A self-venting vessel system according to claim 2 wherein said urging means comprises:
    a threaded opening in said flexible frame
    a threaded bolt that draws said flexible frame against said vessel and said vessel and lid against each other.

4. A self-venting vessel system according to claim 3 wherein said threaded opening is in the portion of said flexible frame adjacent said lid and said threaded bolt bears against said lid.

5. A self-venting vessel system according to claim 3 wherein said threaded opening is in the portion of said flexible frame opposite from said lid and said threaded bolt bears against the bottom of said vessel.

6. A self venting vessel system according to claim 1 wherein said flexible frame comprises a plurality of portions that can be urged together in a manner that urges said frame against said vessel and urges said lid and said vessel against each other.

7. A self venting system according to claim 1 and further comprising:
    a source of microwave radiation;
    a cavity in communication with said source; and
    a plurality of said vessels and said flexible frames in said cavity.

8. A self venting sealable vessel system for microwave assisted chemistry and comprising:
    a vessel having an inner liner formed of a microwave-transparent chemically resistant material and a pressure-resistant reinforced outer sleeve, with one end of said inner liner forming an opening for placing materials inside said vessel;
    a lid formed of said microwave-transparent chemically resistant material for being seated against said opening and for closing said vessel;
    a stiffening member for being externally seated against said lid;
    a flexible frame surrounding said vessel and lid and formed of a microwave-transparent material; and
    means for urging said frame against said vessel and said stiffening member with a predetermined force to seal said vessel at pressures at or below said predetermined force and so that said frame refrains from flexing until the pressure inside said vessel exceeds said predetermined force, after which said frame flexes sufficiently to allow said stiffening member and said lid to unseat and gases to vent safely from said vessel without rupturing said vessel or said frame.

9. A self venting vessel system according to claim 8 wherein said microwave transparent chemically resistant material comprises a tetrafluoroethylene polymer.

10. A self venting vessel system according to claim 8 wherein said liner is formed of glass.

11. A self venting vessel system according to claim 8 wherein said liner is formed of quartz.

12. A self venting vessel system according to claim 8 wherein said lid is formed of an engineering plastic.

13. A self venting vessel system according to claim 8 wherein said outer sleeve comprises braided fiberglass yarns.

14. A self venting vessel system according to claim 8 wherein said frame is selected from the group consisting of high strength thermoplastic polymers and engineering polymers.

15. A self venting system according to claim 8 and further comprising:

a source of microwave radiation;

a cavity in communication with said source; and a plurality of said vessels and said flexible frames in said cavity.

16. A self venting vessel system according to claim 8 wherein said liner is formed of a perfluoroalkoxy resin.

17. A self venting vessel system according to claim 8 wherein said outer sleeve comprises a polyetherimide resin.

* * * * *